United States Patent [19]

Liu et al.

[11] Patent Number: 4,824,967

[45] Date of Patent: Apr. 25, 1989

[54] PROCESS FOR THE PREPARATION OF 2-PYRROLIDONE

[75] Inventors: Kou-Chang Liu, Wayne; Paul D. Taylor, West Milford, both of N.J.

[73] Assignee: GAF Corporation, Wayne, N.J.

[21] Appl. No.: 211,941

[22] Filed: Jun. 27, 1988

[51] Int. Cl.$^4$ ............................................. C07D 201/08
[52] U.S. Cl. ..................... 548/554; 548/543; 548/552
[58] Field of Search .................. 548/543, 552, 554

[56] References Cited

U.S. PATENT DOCUMENTS 3,136,780  6/1969  Kolyer et al. ............... 548/554
3,140,294  7/1964  Kolyer .......................... 548/554

FOREIGN PATENT DOCUMENTS 636757  5/1963  Japan ............................ 548/554

Primary Examiner—David B. Springer
Attorney, Agent, or Firm—Marilyn J. Maue; Joshua J. Ward

[57] ABSTRACT

This invention relates to an improved process for reacting butyrolactone and ammonia which comprises conducting the reaction in the vapor phase in the presence of a magnesium silicate catalyst to selectively produce 2-pyrrolidone in higher yield and purity.

15 Claims, No Drawings

PROCESS FOR THE PREPARATION OF 2-PYRROLIDONE

BACKGROUND OF THE INVENTION

Current commercial processes for the preparation of 2-pyrrolidone (2-pyrol) are carried out at liquid phase, high pressure e.g. 1900–2500 psig. This process results in a product yield of between 75 and 85 wt. %, about 10% of starting material being lost to the by-product residue which is primarily a dehydrated 2-pyrol dimer, 4-(N-pyrrolidonyl) butyramide, referred to herein as PBA. This liquid phase reaction, carried out at high temperature and pressure, is described by equations I and II.

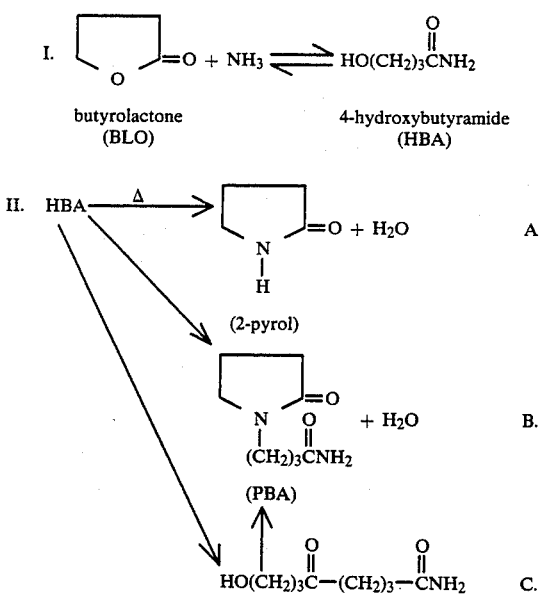

The formation of significant amounts of PBA impurity in current processes unavoidably occurs since the ratio of reaction rates of A and B are more or less fixed at a given concentration of HBA intermediate. Reduction of by-product in the mixture has been attempted by varying the temperature and pressure with little or no effect. High dilution of the reaction mixture may circumvent the problems; however, this remedy is not commercially attractive since significantly larger reactor capacity is required and added costs are incurred by diluent separation.

Accordingly, it is an object of this invention to provide a process resulting in a materially improved yield and purity of 2-pyrol which is commercially feasible and economical.

Another object of this invention is to minimize the formation of PBA as a major contaminant of the system.

Still another object is to provide a process which eliminates the need for oversized reactor capacity.

These and other objects of the invention will become apparent from the following description and disclosure.

THE INVENTION

In accordance with this invention, there is provided a vapor phase process wherein butyrolactone is reacted with ammonia in the presence of a magnesium silicate catalyst, which reaction is operated at a temperature between about 230° C. and about 300° C., preferably between about 250° C. and about 290° C., under a pressure of from about 50 to about 300 psig, preferably a pressure of from about 60 to about 200 psig. In the reaction, a mole ratio of $NH_3$ to BLO between about 1:1 and about 100:1, preferably between about 1.1:1 and about 10:1 is employed. The reaction is conveniently effected in fixed bed reactor packed with the magnesium silicate catalyst in granular form having a particle diameter of from about 1/16 to about ½ inch or a particle size which permits a liquid hourly space velocity (LHSV) of reactants through the reactor at a rate of between about 0.005 and about 0.5, preferably a rate of between about 0.01 and about 0.1.

Generally, the aqueous solution of butyrolactone is introduced into an initial contacting or preheating zone where it is reacted with ammonia to produce HBA. The mole ratio of butyrolactone to water in the feed can range from about 5:1 to about 1:2 although ratios between about 4:1 and about 2:1 are most desirable.

In the contacting zone the feed is heated to pre-reaction temperature, e.g. between about 190° C. and about 200° C. and equilibrium between HBA and $BLO-NH_3$ is established. To assure good mixing, and uniform heating, the contact zone can be packed with glass beads and/or other suitable inert packing material such as glass wool, steel wool, or other fiberous or particulate inert materials, although a mixing valve or impinging gas streams can also be employed, if desired.

The resulting equilibrated reaction mixture is then passed into the reaction zone packed with the magnesium silicate catalyst particles maintained at the reaction temperature of between about 225° C. and about 310° C.

The magnesium silicate catalyst of the present invention comprises between about 10 and about 40 wt. % of magnesium oxide, between about 40 and about 80% silica and may additionally contain between about 0.01 and about 5% by weight of elemental calcium, copper, nickel, potassium or sodium or mixtures thereof and between about 0.01% and about 5% by weight of halogen or sulfate, i.e. Cl, Br, F or $SO_4$. This catalyst composition is ideally suited to the present process since it effects high selectivity to the production of the 2-pyrol product, e.g. above 90%, and minimizes PBA formation thus significantly reducing product entrainment in the undesirable by-product phase. Under the conditions of operation, the present catalyst has a long catalyst life in excess of 1,000 hours. Finally, the catalyst in the present system has high heat stability so that it can be easily regenerated in the presence of nitrogen and air to burn off contaminant coating at a temperature of between about 300° and about 500° C. more often at a temperature of from about 350° C. and about 450° C. However, conditions should be chosen to avoid catalyst structure alteration during regeneration. For best results, it is recommended that, when the selective conversion to 2-pyrol falls below about 90%, the feed of reactants is discontinued and the catalyst is reactivated by oxidation with an air in admixture with nitrogen diluent.

In the reaction zone the butyrolactone and ammonia react in the gas phase with high selectivity to the 2-pyrol product such that yields and purity above 95% are achievable. The hot gaseous product mixture is then passed through a cooling zone wherein it is cooled to a temperature in excess of the PBA condensation temperature, e.g. to between about 100° and about 200° C. depending on pressure which is usually maintained at from about 10 to about 100 psig. The cooled mixture is then passed to a receiver wherein excess ammonia and steam is removed as a vapor and the remaining liquid is subjected to distillation for separation from light and heavy ends which represent a significantly reduced amount of by-product. The cooling zone can be packed with glass beads, or other inert packing material as described above for the contacting zone to enhance more rapid and uniform decrease in temperature.

Excess ammonia vapor and steam separated from the product mixture can be directly recycled to the ammonia feed, if desired.

Having thus generally described the invention, references now had to the accompanying examples which illustrate preferred embodiments thereof but which are not to be construed as limiting to the scope of the invention as more broadly described above and in the appended claims.

The following examples A through C are presented for comparative purposes and describe the operation of previous processes employing the conventional liquid phase reaction.

EXAMPLES A TO C

In a non-catalytic liquid phase high pressure process, operating at about 300° C. and 2,000 psig butyrolactone and ammonia in a mole ratio of 1:1.1 are reacted. After one hour the reaction mixture is cooled and recovered as the product of the process. The product mixture contained 2-pyrol product together with low boiling materials which were distilled off at a temperature of about 105° C. at 40 mm Hg and heavy residue bottoms containing PBA dimer and other high boiling materials, e.g. polymer, together with some entrained product. Three separate runs were effected under the above conditions and the products analyzed by gas chromotography, high pressure liquid chromotography and Kugelrohr distillation. The results of these analysis are reported in following Tables I and IA.

TABLE I

| ANALYSIS OF CRUDE 2-PYROL | | | |
|---|---|---|---|
| SAMPLE | % 2-PYROL | % HEAVY MATERIAL | % LIGHTS |
| A | 89.4 | 9.6 | 0.9 |
| B | 87.6 | 12.2 | 1.1 |
| C | 89.5 | 8.2 | 0.9 |

TABLE IA

| ANALYSIS OF 2-PYROL HEAVY MATERIAL | | | |
|---|---|---|---|
| SAMPLE | % 2-PYROL | DIMER | OTHERS* |
| A | 17% | 41% | 42% |
| B | 18% | 40% | 42% |
| C | 25% | 36% | 39% |

*non-distillable liquids including polymer

The following examples illustrate the process of the invention using a continuous vapor phase reaction in the presence of a magnesium silicate catalyst having the following composition:
MgO=15-20% by weight
SiO$_2$=65-70% by weight
Na=1.5% by weight
Cl=0.05% by weight
SO$_4$=1% by weight

EXAMPLE D

Into a stainless steel tubular reactor having an inner diameter of about 1 inch and a length of 36 inches was introduced 164 g. of the above catalyst particles of about ⅛ inch average diameter. The top 2 inch portion of the tube above the reactor nearest the BLO and ammonia feed inlets was packed with glass beads followed by a 1 inch packing of steel wool, which total 3 inch portion defines a contacting zone where feed was heated and intermixed to equilibrate the reactants. A 3 inch bottom portion below the tubular reactor was similarly packed to allow cooling of the reaction mixture exiting from the reaction zone.

The reactor was purged with nitrogen gas and a heating mantle was placed around the outer surface of the reactor. In the continuous operation, an aqueous solution containing 50 weight % of BLO was introduced into the contacting zone using a precision metering piston pump. Ammonia gas was introduced separately and mixed with BLO/H$_2$O at a temperature of about 200° C. A BLO:NH$_3$ mole ratio of 1:1.1 was maintained by controlling the ammonia flow with a needle valve. The intermixed feed was then passed through the magnesium silicate packed column where at LHSV of 0.01 and a temperature of between 260° and 270° C. under a pressure of 75 psig, cyclization of HBA took place. The temperature in the reaction zone was maintained by the heating mantle surrounding the reaction tube.

The reaction mixture exiting from the magnesium silicate fixed bed, was passed into a cooling zone packed with steel wool and glass beads wherein the temperature reduced to about 180° C. From the cooling zone, the reaction mixture was passed to a stainless steel receiver from which excess ammonia vapors were vented and wherein crude liquid product collected. The crude liquid product, at about room temperature, was then adjusted to distillation for removal of heavy end by-products and the 2-pyrrolidone was analyzed for yield and purity.

In the above operation, the conversion of BLO to 2-pyrrolidone was 96% and the product was above 97% pure with less than 2% of heavy residue. Product analysis was made by gas chromatography, high pressure liquid chromatography, and Kugelrohr distillation.

EXAMPLES 1-9

Catalyst Screening

The reaction of Example D was repeated for each of the following, except that the various catalysts shown in Table II were substituted for the magnesium silicate. Also, some of the runs were conducted in a reactor of 1 inch inner diameter and length of 12 inches at LHSV of 0.03 (reactor 1). The remaining runs were conducted in a reactor of 1 inch inner diameter and length of 36 inches at LHSV of 0.01 (reactor 2). Sample analyses were performed on a Perkin-Elmer Sigma I gas chromatograph equipped with 0.5 mm thick DB5 coated on 0.32 mm×25 meter capillary column. The injection port and detector were set at 250° C. and oven temperature was programmed from 80° to 200° C. The results of these runs are as reported in following Table II.

TABLE II

| Example # | Catalyst description | Temperature (°C.) | Feed Rate (g/hr.) | Reactor Type | Conversion of BLO (wt. %) | % Selectivity To 2-Pyrol | 2-Pyrol wt. % Yield |
|---|---|---|---|---|---|---|---|
| 1 | Alumina | 250 | 4 | 2 | 58 | 71 | 41 |
| 2 | 3.6% Nickel Sulfate on pumice | 250 | 4 | 2 | 10 | 4 | 4 |
| 3 | Pumice Stone | 240 | 3 | 2 | 7 | 50 | 4 |
|   |   | 340 | 3 | 2 | 41 | 86 | 35 |
| 4 | 10% KCl on Alumina | 250 | 5 | 1 | 45 | 75 | 34 |
|   |   | 300 | 5 | 1 | 79 | 70 | 55 |
| 5 | 10% MgSO4 on Alumina | 250 | 5 | 1 | 83 | 84 | 70 |
| 6 | 10% Zinc oxide on Zeolon (Zeolite) | 250 | 6 | 1 | 25 | 60 | 15 |
| 7 | 11% Copper oxide on Alumina (Girdler T317) | 250 | 4 | 1 | 71 | 68 | 48 |
| 8 | Chromia on Alumina (Girdler G41) | 250 | 4 | 1 | 53 | 70 | 37 |
| 9 | Magnesol* | 250 | 4 | 1 | 94 | 96 | 90 |

*Magnesium silicate supplied by Reagent Chemical & Research Inc.; Surface Area = 400–550 m$^2$/g Contains 14.5 wt % MgO and 65–70 wt % SiO$_2$

EXAMPLE 10

Catalyst Life

In order to study the life of the catalyst, the magnesol catalyzed vapor phase process outlined in Example D was operated continuously for more than 700 hrs in reactor 2. under the conditions including a reaction temperature of 250° C.; a pressure of 75 psig.; feed weight ratio of BLO/Water/NH$_3$ of 1:1:2 and a LHSV of 0.01. The yields, measured by Glc (gas chromatograph) for 2-pyrol, and PBA, are shown in Table III.

TABLE III

MAGNESOL CATALYZED VAPOR PHASE 2-PYROL PROCESS - 25% BLO + 25% WATER + 50% NH$_3$ FEED

| Example # | Run Time (Hrs.) | 2-Pyrol (wt. %) | PBA (wt. %) |
|---|---|---|---|
| 10 a | 18 | 98.8 | — |
| 10 b | 43 | 98.3 | — |
| 10 c | 72 | 98.1 | — |
| 10 d | 121 | 98.2 | — |
| 10 e | 188 | 97.5 | — |
| 10 f | 241 | 97.0 | 0.09 |
| 10 g | 288 | 95.5 | 0.47 |
| 10 h | 384 | 96.4 | 0.45 |
| 10 i | 649 | 96.5 | 0.92 |
| 10 j | 744 | 96.3 | 0.93 |
| 10 k | 785 | 96.4 | 0.58 |

EXAMPLE II

The process of Example 10 was repeated in the presence and absence of water. Thus, BLO reactant in Samples 1–6 were undiluted while in Samples 7–16 a 50/50 BLO-water mixture was employed. The results of these runs are as reported in following Table IV.

TABLE IV

| Sample | Feed | Run Time, Hr. | % BLO Conversion | % Selectivity to Product | % 2-Pyrol Yield |
|---|---|---|---|---|---|
| 1 | 100% BLO | 18.5 | 95 | 90.5 | 86.1 |
| 2 |   | 26.5 | 92 | 88 | 81.3 |
| 3 |   | 41.5 | 86 | 88 | 75.6 |
| 4 |   | 49 | 92 | 89 | 82.2 |
| 5 |   | 67 | 81 | 86 | 70 |
| 6 |   | 89.5 | 79 | 86 | 67.9 |
| 7 | 50% BLO/ 50% H$_2$O | 93 | 80 | 87 | 69.5 |
| 8 | 50% BLO/ 50% H$_2$O | 97.5 | 82 | 92 | 75 |
| 9 | 50% BLO/ 50% H$_2$O | 125 | 94 | 96 | 90.8 |
| 10 | 50% BLO/ 50% H$_2$O | 142 | 96 | 95 | 91.3 |
| 11 | 50% BLO/ 50% H$_2$O | 168 | 98 | 96 | 93.8 |
| 12 | 50% BLO/ 50% H$_2$O | 184 | 97 | 97 | 93.6 |
| 13 | 50% BLO/ 50% H$_2$O | 191 | 96 | 97 | 92.8 |
| 14 | 50% BLO/ 50% H$_2$O | 207 | 96 | 96 | 92.2 |
| 15 | 50% BLO/ 50% H$_2$O | 215 | 96 | 96 | 92.4 |
| 16 | 50% BLO/ 50% H$_2$O | 231 | 97 | 96 | 93.1 |

The above date shows that by changing the feed from 100% BLO to a 50% aqueous BLO solution, the selectivity for 2-pyrol yield is dramatically increased. The experiment was carried out at 250° C., 75 psig, with NH$_3$/BLO ratio of about 50 to 1. The improvements of selectivity by addition of water to the BLO feed was clearly demonstrated.

It is to be understood that many alterations and modifications can be made in the above examples without departing from the scope of the invention. For example, the dilution of BLO reactant can be reduced to as low as 0.5% while still providing the improvements of the invention. Also any ratio of MgO to SiO$_2$ within the above ranges can be substituted in the examples to provide product in high yield and selectivity. Additionally, the process can be carried out in a batch or continuous manner without loss of product yield or quality.

What is claimed is:

1. The process which comprises reacting butyrolactone with ammonia in the vapor phase at an elevated temperature and pressure in the presence of a magnesium silicate particulate catalyst which catalyst optionally contains between about 0.01% and about 5% by weight of elemental Ca, Cu, Ni, K, Na or mixtures thereof and between about 0.01% and about 5% by weight of Cl, Br, F or So$_4$ groups and reacting said components for a period sufficient to produce 2-pyrrolidone in high yield and selectivity.

2. The process of claim 1 wherein said butyrolactone is reacted with ammonia gas at a temperature between about 225° C. and about 310° C. under a pressure of from about 50 psig to about 300 psig.

3. The process of claim 2 wherein said butyrolactone is reacted with said ammonia gas at a temperature between about 250° C. and about 290° C. under a pressure of from about 60 psig. to about 200 psig.

4. The process of claim 1 wherein the mole ratio of ammonia to butyrolactone is between about 1:1 and about 100:1.

5. The process of claim 1 wherein the reaction is effected in a reactor packed with a fixed bed of said magnesium silicate particles and liquid hourly space velocity of reactants through the reactor is between about 0.005 and about 0.5.

6. The process of claim 5 wherein the liquid hourly space velocity of reactants through the reactor is between about 0.01 and about 0.1.

7. The process of claim 5 wherein said magnesium silicate granules have an average particle diameter of from about 1/16 to ½ inch.

8. The process of claim 1 wherein said butyrolactone is first contacted with said ammonia in a preheating zone operated at a temperature between about 190° C. and about 200° C. and said butyrolactone is introduced into said preheating zone as an aqueous solution wherein the mole ratio for butyrolactone to water is between about 5:1 and about 1:2.

9. The process of claim 8 wherein said mole ratio of butyrolactone to water is between about 4:1 and about 2:1.

10. The process of claim 8 wherein the mole ratio of ammonia to butyrolactone is between about 1.1:1 and about 10:1.

11. The process of claim 1 wherein said magnesium silicate catalyst contains between about 10 wt. % and about 40 wt. % of magnesium oxide and between about 40 wt. % and about 80 wt. % silicon oxide.

12. The process of claim 1 wherein said reaction is effected in a continuous manner the catalyst is disposed as a particulate fixed bed and the reactants are continuously passed through said catalyst bed until the conversion of butyrolactone falls below 90% at which time the reaction is interrupted and the catalyst is reactivated.

13. The process of claim 12 wherein the deactivated catalyst is regenerated with a nitrogen and air mixture at a temperature of from 300° C. to 450° C.

14. The process of claim 1 wherein the reaction mixture containing 2-pyrrolidone product from the reaction zone is passed to a cooling zone wherein it is cooled to a temperature above the condensation temperature of by-product PBA and any excess ammonia and steam gas is removed and is optionally recycled to the system and the product is recovered in the liquid phase.

15. The process of claim 14 wherein the product is recovered from the liquid phase by distillation.

* * * * *